United States Patent [19]
Hofmann et al.

[11] Patent Number: 5,283,036
[45] Date of Patent: Feb. 1, 1994

[54] APPARATUS FOR COUPLED LIQUID CHROMATOGRAPHY AND NUCLEAR MAGNETIC RESONANCE SPECTROSCOPY MEASUREMENTS

[75] Inventors: Martin Hofmann, Rheinstetten; Manfred Spraul, Ettlingenweier, both of Fed. Rep. of Germany

[73] Assignee: Bruker Analytische Messtechnik GmbH, Fed. Rep. of Germany

[21] Appl. No.: 831,775

[22] Filed: Feb. 5, 1992

[30] Foreign Application Priority Data

Feb. 11, 1991 [DE] Fed. Rep. of Germany ....... 4104075

[51] Int. Cl.$^5$ ..................... B01D 15/08; G01N 30/02; G01N 24/08
[52] U.S. Cl. ......................................... 422/70; 422/81; 436/161; 436/173; 324/321; 210/198.2; 210/659; 73/61.59; 73/864.83
[58] Field of Search ................... 422/70, 81, 63, 82, 422/103; 436/161, 173; 73/864.83, 864.84, 61.59; 324/321; 210/656, 659, 198.2

[56] References Cited

U.S. PATENT DOCUMENTS

| | | | |
|---|---|---|---|
| 3,690,833 | 9/1972 | Ferrari | 73/61.59 |
| 3,731,539 | 5/1973 | Brittan et al. | 73/864.83 |
| 3,999,439 | 12/1976 | Munk | 73/864.83 |
| 4,123,236 | 10/1978 | Hirschfeld et al. | 73/23.27 |
| 4,386,054 | 5/1983 | Takeuchi et al. | 436/173 |
| 4,577,492 | 3/1986 | Holba et al. | 422/70 |
| 4,581,583 | 4/1986 | Van Vliet et al. | 324/321 |
| 5,006,315 | 4/1991 | Maroulis et al. | 436/161 |
| 5,008,204 | 4/1991 | Stehling | 436/161 |
| 5,096,826 | 3/1992 | Barbic et al. | 436/173 |

FOREIGN PATENT DOCUMENTS 2175093 11/1986 United Kingdom .

OTHER PUBLICATIONS

Bayer et al, "On-line Coupling of HPLC and NMR" J. Chrom. 186 (1979) 497-507.
Grimaldi et al. "Stopped Flow NMR Spectroscopy" J. Amer. Chem. Soc. (USA) vol. 94 No. 22, pp. 7641-7645, 1972.

*Primary Examiner*—James C. Housel
*Assistant Examiner*—Jan M. Ludlow
*Attorney, Agent, or Firm*—Walter A. Hackler

[57] ABSTRACT

Apparatus is provided for coupled liquid chromatography and nuclear magnetic resonance (NMR) spectroscopy measurements. The apparatus includes a liquid chromatograph, an intermediate storage device for intermediately storing of components of a probe eluent and an NMR spectrometer. Selected intermediately stored components are fed to an NMR measurement unit. The intermediate storing device includes a number of capillary tubes, which are switchable by an automatically controlled valve arrangement for selectively receiving and delivering desired eluent components.

12 Claims, 3 Drawing Sheets

APPARATUS FOR COUPLED LIQUID CHROMATOGRAPHY AND NUCLEAR MAGNETIC RESONANCE SPECTROSCOPY MEASUREMENTS

BACKGROUND OF THE INVENTION

The present invention relates to a process and an apparatus for coupled liquid chromotography and nuclear magnetic resonance (NMR) spectroscopy measurements whereby components of a sample were detected and separated using liquid chromotography and whereby these components were measured afterwards using nuclear resonance spectroscopy.

Such a process and such an apparatus are known, for example from J. Chromatography 186, 497, (1979), "On-line Coupling of High-Performance Liquid Chromatography and Magnetic Resonance".

In a pure on-line coupling, the NMR-spectrometer is directly coupled after the liquid chromatograph.

During the HPLC-measurement (HPLC equals High Performance Liquid Chromatography) of a continuous-flow process, the eluent and the resulting peaks are fed continuously and sequentially into the NMR-spectrometer to be spectrometrically examined "on-line" therein.

As an alternative to the continuous-flow-process the stop-flow technique is used, whereby the flow pump delivers the eluent only during certain time periods. The flow pump stops as long as a component is inside the NMR-spectrometer.

The obtained NMR signal sensitivity in dependence on the concentration of the pertinent component can be insufficient with the continuous-flow process, since the retention time in the NMR measuring head is limited.

The obtained chromatographical separation efficiency for the subsequent components, which are still in the separation column, is deteriorated in the stop-flow process because of diffusion.

SUMMARY OF THE INVENTION

A sample to be measured can be composed of a large number of components. The present invention is based on the objective, to provide a process and an apparatus for coupled liquid chromatography and nuclear magnetic resonance spectroscopy measurements, in which a separation of the components is realized before the nuclear resonance spectroscopy measuring and which allows a continuous-flow process as well as a stop-flow process during NMR spectroscopy.

As a solution of this objective, the present invention provides an automatized process in which the separation of the sample using chromatography works continuously.

Chromatographically separated components can be fed on-line into the NMR spectrometer through a line or they can be stored in intermediate stores. From here, they are feedable into the NMR spectrometer at any time without transfusing and without manual intervention through the same line. This process allows a stop-flow operation of the NMR spectrometer having an arbitrary measuring time duration without effecting negatively the chromatograpical separation efficiency by longer stopping times.

Preferably, the chromatographically separated components were deteced by a LC-detector (i. e. UV/VIS or RI, respectively) and, thereby, their intermediate storage will be arranged. Fractions of the eluent which are not of interest, are fed into a waste collecting container.

An apparatus, solving the above mentioned objective, is characterized in that a device for intermediate storage includes several storage capillaries in which each capillary is capable of receiving one component, thereby separating locally the components into the capillaries.

Preferably, the capillaries of the intermediate storage device have different lengths, according to different volumes of NMR measuring heads.

Controllable valve arrangements are preferably inserted respectively before and after the intermediate storage device for feeding the components of the sample into a selected capillary or for feeding the contents of any capillary into the measuring head of the NMR spectrometer, respectively.

The mentioned valve arrangements are preferably power-driven multiple-way turning valves, as known in the art, whereby the valve position and the turning direction of the selector turning valve is provided by corresponding commands of an evaluating and control unit.

The present invention allows an advantageous coupled measurement between liquid chromatography and nuclear resonance spectroscopy, because the measurement is flexible and precisely controllable.

BRIEF DESCRIPTION OF THE DRAWINGS

The invention is described below in more detail in preferred embodiments with reference to the drawings in which.

DESCRIPTION OF THE PREFERRED EMBODIMENT(S)

Figure 1:
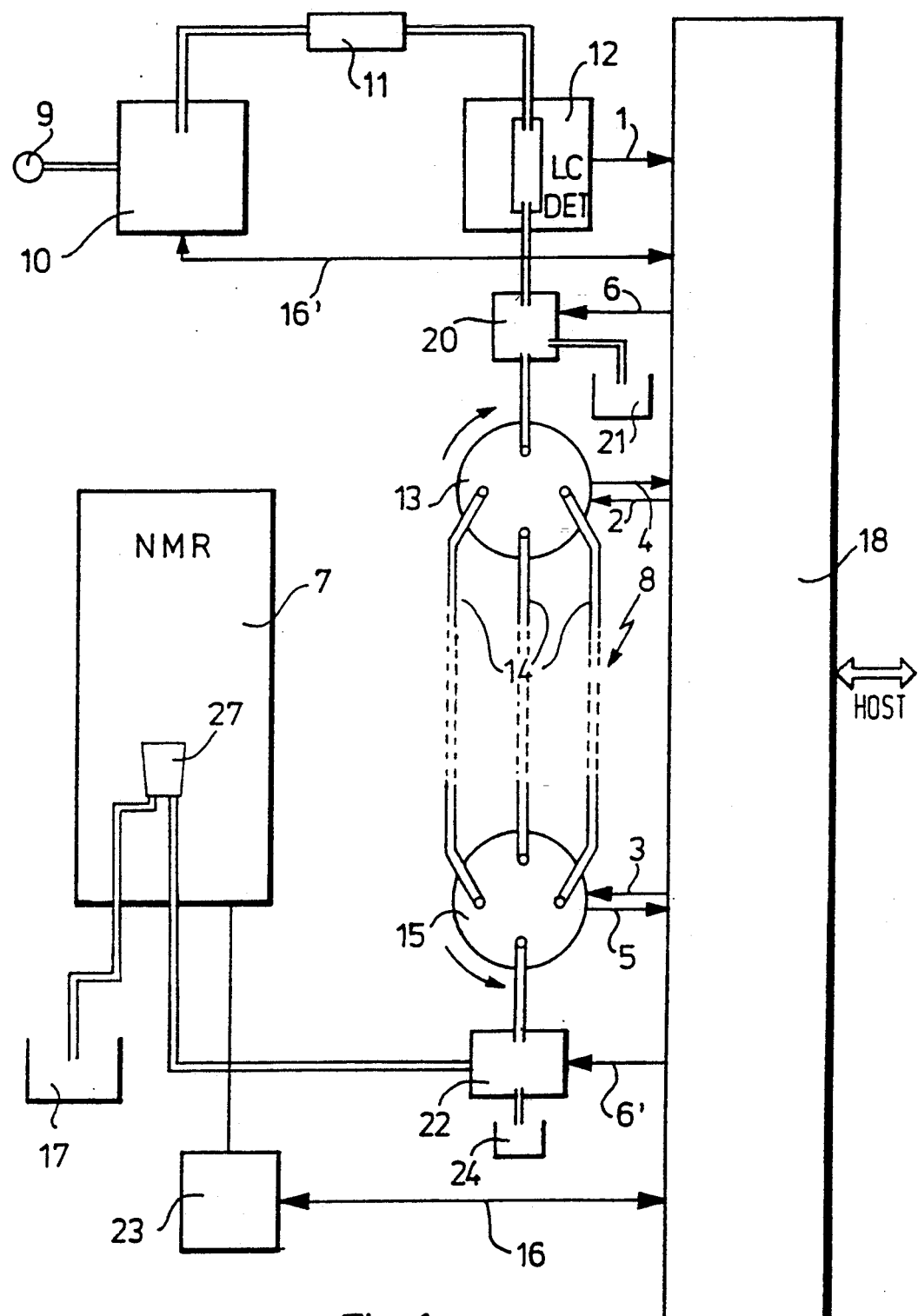
FIG. 1 shows a first embodiment of the present invention.

First of all, the process according to the present invention is explained using FIG. 1, which shows a schematic basic structure of a first embodiment of the present invention.

A sample eluent which is fed into an input 9 will be pumped by a LC-pump 10 into a LC-column 11 and fractioned therein. The fractioned sample eluent will be supplied from the LC-column 11 into a LC-detector 12, which is generally working in the UV/VIS range. Therein, the LC peak detection will be executed. The LC-detector supplies an evaluating and control unit 18 with a detector signal 1. (LC equals Liquid Chromatography). The evaluating and control unit 18 evaluates among others the flow rate of the sample and the times of the peak measurement (retention) and puts them into relation. An intermediate storage device 8 is coupled after the LC detector 12 and with multiple-way turning valves 13 and 15 at its input and output sides, respectively.

The multiple-way turning valves 13 and 15 are controlled by the evaluating and control unit 18 according to the retentions so that the desired components can be distributed to each of capillaries 14 of the intermediate storage device 8 and desired components can be picked up by the multiple-way turning valve 15 at the output side of the intermediate storage device 8 for measurement by a subsequent NMR spectrometer 7. Thereby, a flexible and selective sequential connection of respectively elected capillary 14 of the intermediate storage device is realized for the subsequent measurement by the NMR spectrometer 7. After finishing the measurement in the NMR spectrometer 7 the components are forwarded into a waste collecting container 17.

Figure 3:
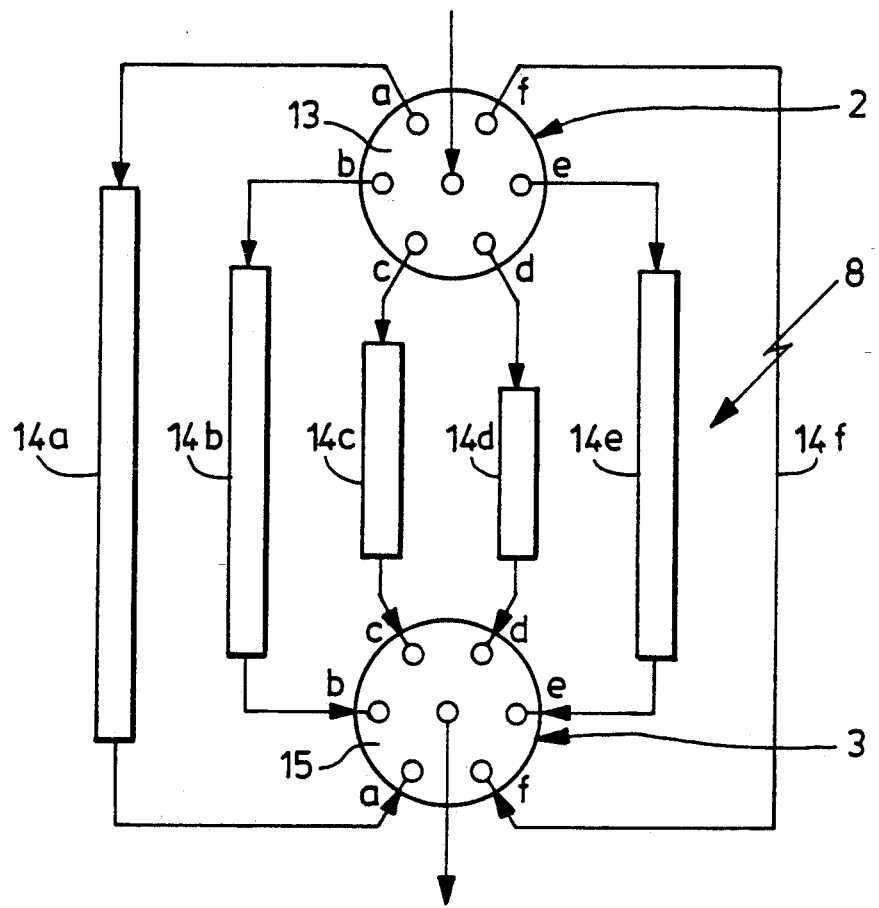
FIG. 3 shows details of a preferred intermediate storage device which is usable with the present invention.

The intermediate storage device 8, as shown in FIG. 1 in combination with the multiple-way turning valves, 13 and 15 can be designed as shown in FIG. 3. The capillaries 14a, 14b, 14c, 14d, 14e and 14f as shown therein may have different capacities and lengths, respectively. In general, all capillaries of one set have the same length and capacity, respectively, according to the size of the used NMR measuring head 27. For a NMR measuring head having a different size the whole set of capillaries of the intermediate storage device will be exchanged. Exceptionally, as shown in FIG. 3, capillaries of different length can be used within one set. The multiple-way turning valves are driven by pulse motors, which receive control signals 2 and 3 from the evaluating and control unit 18. Preferably, valve position signals 4 and 5 for indicating the present position of the multiple-way turning valves 13 and 15 are led to the evaluating and control unit 18 for an independent operation of the multiple-way turning valves 13 and 15.

The arrangement, as shown in FIG. 1, has an input of the intermediate storing device 8 from LC detector 12 and an output leading to NMR spectrometer 7.

For someone skilled in the art, it is obvious that such an intermediate storage device can also be configurated differently, for example, with one input and several outputs, i.e. for simultaneously, preferably in parallel, measurement of different peaks by in parallel arranged different spectrometers, or with one output and several inputs, whereby for example, to the input from the LC detector 12 another input is provided, being supplied with a reference fluid as frequency standard, preferably $D_2O$.

The intermediate storage device as shown in FIG. 1 is single staged configurated.

However, the process according to the present invention, is also suitable for a multiple staged intermediate storage device.

In addition to the multiple-way turning valves 13 and 15 arranged before and after the intermediate storage device, first and second controllable valves 20 and 22 are provided in the flow path of the sample. The first controllable valve 20 is a three-way-valve being coupled with its input to the output of the LC detector 12, with a first output to the first multiple-way turning valve 13 and with a second output to a second waste collecting container 21 for leading sample fractions into the waste container, said sample fractions being no longer usable for the following NMR spectroscopy measurement. The second multiple-path turning valve 15 is followed by a second controllable valve 22, being also a three-way-valve for connecting the intermediate storage device 8 with the waste collecting container 24 or for leading a component into the NMR spectrometer 7, respectively. The first and second controllable valves 20 and 22 are controlled by the evaluating and control unit 18 via signal lines 6 and 6'.

Additionally, an automatic start-stop unit 23 is provided in the embodiment according to FIG. 1 for using a start-stop measuring process in connection with the other valve units. The start-stop unit 23 communicates with the evaluating and control unit 18 via a signal line 16. The start-stop unit 23 in combination with the multiple-way turning valves 13 and 15 being controlled by the control signals 2 and 3, as well as the first and second controllable valves 20 and 22, which are controlled by the evaluating and control unit 18 via the control signals 6 and 6' provide a start-stop process without the danger of diminishing the chromatographical separative effectiveness.

A preferred embodiment of the process according to the present invention will be exemplarily described below having an arrangement according to FIG. 1.

The evaluating and control unit 18 evaluates among others the flow rate of the eluent, which is either known and memorized or which is measured, respectively. The evaluation of the detector signal 1 indicates the appearance of chromatographical peaks, e.g. the LC detector 12 is passed in this moment by a component of the sample. Using a predetermined algorithm, the evaluating and control unit 18 decides whether the measured peak is related to a pertinent component. As long as no peak is measured or the measured peak is not pertinent, respectively, the eluent is forwarded via the first three-way controllable turning valve 20 into a waste collecting container 21 after passing the LC detector 12. However, as soon as a relevant peak is detected, the unit 18 gives a command via a line 6 for switching the valve 20, thereby ensuring that the sample eluent is led into the intermediate storage device 8, which is coupled with the multiple-way turning valves 13 and 15 at its input and output sides, respectively. A command to valve 13 via line 2 ensures that the sample eluent is forwarded into a selected capillary 14 of the intermediate storage device 8. The sample passes this capillary and reaches first of all the waste collecting container 24 via the second multiple-way turning valve 15 and the second controllable valve 22. The waste collecting container 24 can be identical with container 21. The valves 20, 13 and 22, 15, respectively, can be integral. Heretofore, it shall be noted that the whole line system of the arrangement according to FIGS. 1 and 2, respectively, is filled with eluent before measuring. The eluent passing into the collecting container 24 therefore contains no pertinent component. Because the evaluating and control unit 18 is aware of the flow rate and, furthermore, continuously receives the detected signal intensity from LC detector 12, it provides on-line the calculated result, at which time a component which creates a maximum signal at the detector 12, passes capillary 14. As soon as the part of the flowing sample eluent corresponding to the maximum of a pertinent peak flows into capillary 14, the valves 20, 13, 15 and 22 are switched via control lines 6, 2, 3, and 6' for holding this part in the capillary 14. The eluent flows either into collecting container 21 via valve 20 or in another capillary 14 via valve 13, respectively. In this case, eluent is still flowing into collecting container 24 via valve 15 and 22.

By this means, several pertinent components can be stored step by step within the capillaries 14 of the intermediate storage device 8. Thereby, the chromatographical separation in column 11 is never interrupted.

Even while the chromatographical separation and detection is in progress, the NMR measurement can start time independently. To do so, the evaluating and control unit 18 gives control commands to valves 20, 13, 15 and 22 via the lines 6, 2, 5 and 6', so that the content of a selected capillary 14 reaches the measuring head of the NMR spectrometer and new eluent flows from the pump 10 via the column 11 and the LC detector 12. Using the measured or known flow rate, the evaluating and control unit calculates at which time the intermediately stored content of capillary 14 reaches the measuring head of NMR spectrometer 7. At this time, the valves will be reswitched, so that the eluent can reach again waste collecting container 21 directly via valve 20 or can reach waste collecting container 24 by passing the intermediate storage device 8 and valve 15, respectively.

After the pertinent component derived from the capillary 14 is filled in the NMR measuring head, the NMR measuring of this component can be started, for example by using the start-stop unit 23 which communicates with the evaluating and control unit 18 via the signal line 16. Any amount of time is provided for the measurement. Thereby, the signal-to-noise ratio can be improved by accumulation or sophisticated, for example two-dimensional NMR-measurements can be done, respectively.

After the NMR measurement of this component, valves 20, 13, 15 and 22 can be controlled in the above described way for picking another component out of the intermediate storage device. The sample eluent with the previous component is thereby pushed out of the NMR measuring unit and forwarded into a waste collecting container 17, which can be identical with the container 21 and/or 24, respectively; via the signal line 16' a start-stop communication is established to the chromatography pump.

Figure 2:
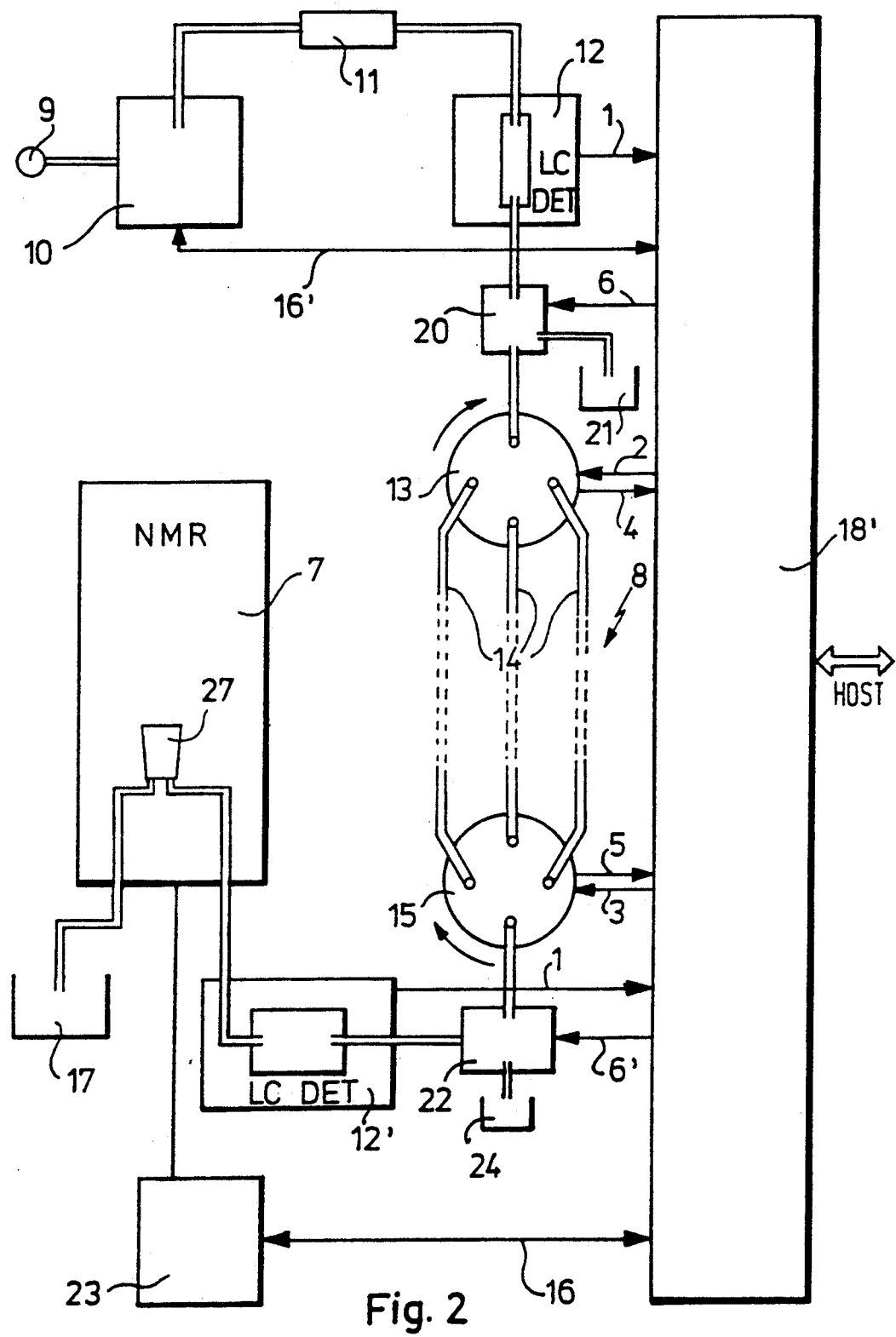
FIG. 2 shows a second embodiment of the present invention having one liquid chromatography detector before and one after the intermediate storage device.

FIG. 2 shows another preferred embodiment of the present invention which is based on the arrangement according to FIG. 1. The embodiment according to FIG. 2 incorporates another LC detector arrangement 12', which is located after the intermediate storage device 8. This second LC detector 12' provides a second detector signal 1' for an evaluating and control unit 18'. With the support of the second LC detector 12', which is located immediately before the entrance of the NMR spectrometer 7 in the embodiment of FIG. 2, it is ensured, that the measuring head of the NMR spectrometer is optimally supplied with the intermediately stored component.

At this location it is also possible, to provide a detector of a different type, instead of the LC detector 12', for example an IR detector or an IR spectrometer, respectively. This enlarges the provided informations from the component to be measured.

The described process and the arrangement shown in FIGS. 1 and 2 have only exemplary character. By using another pump the feeding in of the sample eluent to each of the capillaries 14 and the feeding out therefrom can be done completely independently. This can also be done using only one pump 10, if the chromatographical separation is stopped for a short time and, for example via a direct line to valves 20 or 13, a pure eluent is pumped into the intermediate storage device.

The significant advantages of the present invention are that it is possible to carry out continuous-flow measurements in an automatical measuring process. This is possible by continuously passing sample eluent through a capillary 14 of the intermediate storage device 8. Above all, it is advantageous to enable the same arrangement to also carry out discontinuous NMR spectroscopy measurements, as well as long duration measurements, without disturbing the continuously running process of chromatography. The whole arrangement is closed until the last measurement is done. That means, that the eluent does never get into contact with its environment and never has to be moved or filled manually.

Preferably, both embodiments as shown in FIGS. 1 and 2 use program controlled evaluating and control units 18 and 18', respectively. They are able to communicate with a host computer, as indicated in the drawings.

The described features of the embodiments can independently, as well as in combination, be established in the present invention.

We claim:

1. An apparatus for carrying out coupled liquid chromatography and nuclear magnetic resonance spectroscopy measurements, said apparatus comprising:
   a liquid chromatograph having column means for fractionating an eluent into eluent components and first detector means, positioned downstream of said column, for detecting the eluent components and producing detector signals;
   a nuclear magnetic resonance (NMR) spectrometer including measuring head means for measuring the eluent components detected by the liquid chromatograph;
   an intermediate storage device means, interconnected between said liquid chromatograph and said nuclear magnetic resonance spectrometer, for intermediately storing pertinent components of the eluent complying with predetermined conditions, said storage device means having a plurality of intermediate stores each storing one component of the eluent;
   first multiple way turning valve means, disposed between said first detector means and said intermediate storage device means, for selectively feeding the eluent components into the intermediate stores;
   second multiple way turning valve means, disposed between said intermediate storage device means and said NMR spectrometer, for selectively feeding the eluent pertinent components into the NMR spectrometer; and
   evaluating and control means having an input connected to the first detector means, a first output connected to said first multiple way turning valve, and a second output connected to said second multiple way turning valve, for supplying a first turning valve control signal to successively feed one detected eluent component into one intermediate store, and a second turning valve control signal to successively feed each pertinent stored component into the NMR spectrometer in response to receiving signals from said first detector means.

2. The apparatus according to claim 1, further comprising automatic stop-flow means, communicating with said evaluating and control means, for enabling start-stop operation of the apparatus without diminishing chromatographical separative effectiveness.

3. The apparatus of claim 1, wherein the intermediate stores comprise capillaries.

4. The apparatus of claim 1, wherein the intermediate stores have storage capacities, and the storage capacity of each intermediate store is approximately equal.

5. The apparatus according to claim 1, further comprising a first three-way valve, having an input and two outputs, disposed between the first detector means and said first multiple way turning valve, and a second three-way valve, having an input and two outputs, disposed between said second multiple way turning valve and the NMR measuring head.

6. The apparatus according to claim 5, wherein said evaluating and control means comprises a third output connected to said first three-way valve and a fourth output connected to said second three-way valve, the third output producing a first three-way valve control signal to control said first three-way valve, and the fourth output producing a second three-way valve control signal to control said second three-way valve.

7. The apparatus according to claim 6, further comprising an automatic start-stop means for enabling start-stop operation of the apparatus without diminishing chromatographical separative effectiveness, said start-stop means being connected to said evaluating and control means and to said nuclear magnetic resonance spectrometer.

8. The apparatus according to claim 1, further comprising a second detector means for detecting the eluent components disposed between said second multiple way turning valve and the nuclear magnetic resonance measuring head.

9. The apparatus according to claim 8, wherein said second detector means is selected from the group consisting of an infrared detector and an infrared spectrometer.

10. The apparatus according to claim 8, further comprising a first three-way valve, having an input and two outputs, disposed between the first detector means and said first multiple way turning valve, and a second three-way valve, having an input and two outputs, disposed between said second multiple way turning valve and the NMR measuring head.

11. The apparatus according to claim 10, wherein said evaluating and control means comprises a third output connected to said first three-way valve and a fourth output connected to said second three-way valve, the third output producing a first three-way valve control signal to control said first three-way valve, and the fourth output producing a second three-way valve control signal to control said second three-way valve.

12. The apparatus according to claim 11, further comprising an automatic start-stop means for enabling start-stop operation of the apparatus without diminishing chromatographical separative effectiveness, said start-stop means being connected to said evaluating and control means and to said nuclear magnetic resonance spectrometer.

* * * * *